United States Patent [19]

Russo et al.

[11] 4,446,234
[45] May 1, 1984

[54] VITRO CELLULAR INTERACTION WITH AMNION MEMBRANE SUBSTRATE

[75] Inventors: Raimondo Russo; Lance A. Liotta, both of Bethesda, Md.

[73] Assignee: The United States of America as represented by the Department of Health and Human Services, Washington, D.C.

[21] Appl. No.: 314,477

[22] Filed: Oct. 23, 1981

[51] Int. Cl.³ .................. C12Q 1/29; C12N 5/00; C12M 3/00
[52] U.S. Cl. ................................ 435/29; 435/240; 435/284
[58] Field of Search ............ 435/4, 6, 29, 32, 33, 435/35, 240, 241, 284, 285, 286

[56] References Cited

U.S. PATENT DOCUMENTS 4,308,351 12/1981 Leighton et al. ............... 435/284

OTHER PUBLICATIONS

Hart, I. R., et al., "An In Vitro Quantitative Assay For Tumor Cell Invasion", Cancer Res., 38:3218–3224, 1978.
Mareel, et al., "Characterization of Spontaneous, Chemical and Viral Transformants of C3H/3T3 Type Mouse Cell Line by Transplantation into Young Chick Blastoderms", J. Natl. Cancer Inst., 54:923–929, 1975.
Mareel, et al., "Methods of Study of the Invasion of Malignant C3H-Mouse Fibroblasts into Embryonic Chick Heart in Vitro", Virchows Arch. B Cell Pathol., 30:95–111, 1979.
Pourreau-Schneider, et al., "The Role of Cellular Locomotion in Leukemic Infiltration, an Organ Culture Study on Penetration of L5222", etc., Virchows Arch. B Cell Pathol., 23:257–264, 1977.
Noguchi, et al., "Chick Embryonic Skin as a Rapid Organ Culture Assay for Cellular Neoplasia", Science (Wash, D.C.) 199:980–983, 1978.
Tickle, et al., "Cell Movement and the Mechanism of Invasiveness: A Survey of the Behavior of Some Normal and Malignant Cells Implanted in the Developing Wing", etc., J. Cell Sci. 21:293–322, 1978.
Schirrmacher, et al., "Tumor Metastases and Cell-Mediated Immunity in a Model System in DBA/2 Mice, I. Tumor Invasiveness in Vitro and Metastasis Formation in Vivo", Int. J. Cancer, 23:233–244, 1979.
Schleich, et al., "Patterns of Invasive Growth In Vitro, Human Decidua Graviditatis Confronted with Established Human Cell Lines and Primary Human Explants", J. Natl. Cancer Inst. 56:221–227, 1976.
Pauli, et al., "In Vitro Determination of Tumor Invasiveness Using Extracted Hyaline", Cancer Res., 41:2084–2091, Jun. 1981.
G. Paste, et al., "In Vitro Selection of Murine B16 Melanoma Variants with Enhanced Tissue-Invasive Properties", Cancer Research, 40:1636–1644, May 1980.
Mainardi, et al., "Degradation of (Type IV) Basement Membrane Collagen by a Proteinase Isolated from Human Polymorphonuclear Leukocyte Granules", J. Biol. Chem., 255:5435, 1980.
Liotta, et al., "Metastatic Potential Correlates with Enzymnatic Degradation of Basement Membrane Collagen", Nature, 284:67, 1980.
Beesley, et al., "Granulocyte Migration Through Endothelium in Culture", J. Cell. Sci., 38:237, 1979.

Primary Examiner—Robert J. Warden
Attorney, Agent, or Firm—Holman & Stern

[57] ABSTRACT

Amnion membranes derived from mammalian placentas are employed as the substrate tissue in in vitro assay methods for evaluating cellular interaction with natural barrier tissues. The amnion is also employed as a growth substrate, particularly for the culture of cells difficult to culture on conventional substrates. A diagnostic apparatus including an amnion membrane is also disclosed.

16 Claims, 9 Drawing Figures

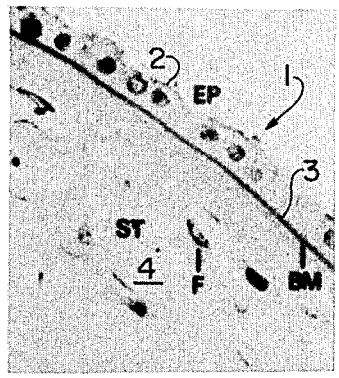
FIG. 1
TRANSMISSION ELECTRON MICROGRAPH OF INTACT HUMAN AMNION (1) (1000x). THE EPITHELIAL CELLS (2)(EP) ARE ATTACHED TO THE CONTINUOUS AMORPHOUS BASEMENT MEMBRANE (3)(BM). THE UNDERLYING AVASCULAR STROMA(4)(ST) CONTAINS LOOSELY BOUND COLLAGEN (TYPE I), NOT IDENTIFIED.
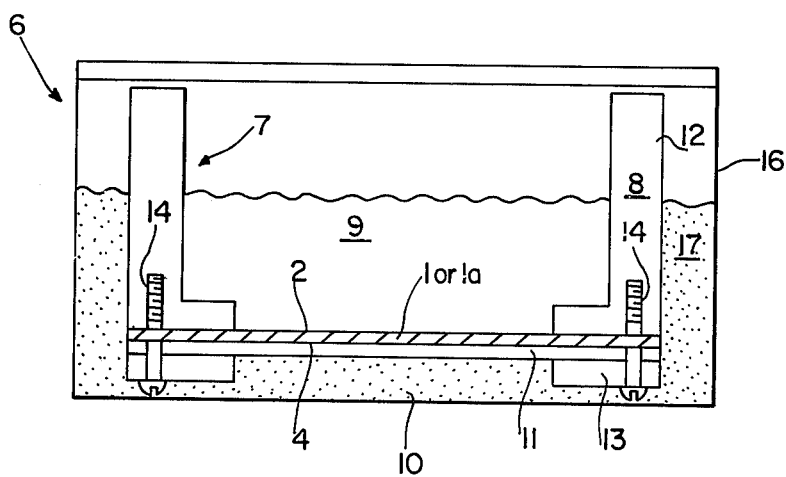

TRANSMISSION ELECTRON MICROGRAPH (4000x) OF
HUMAN AMNION (Ia) DENUDED OF EPITHELIAL CELLS.

PHOTOMICROGRAPH (900x) OF AMNION EPITHELIUM (2) INVADED BY MIGRATING PMN.

PHOTOMICROGRAPH (600x) OF PMN INVADING STROMA COLLAGEN.

PHOTOMICROGRAPHIC (200x) OF BREAST CARCINOMA CELLS COLLECTED AFTER PENETRATION OF THE AMNION.

PHOTOMICROGRAPH (400x) OF TUMOR CELL PENE-
TRATION OF THE AMNION.

RELEASE OF RADIOACTIVITY FROM LABELLED AMNION BASEMENT MEMBRANE BY TUMOR CELLS.

VITRO CELLULAR INTERACTION WITH AMNION MEMBRANE SUBSTRATE

BACKGROUND OF THE INVENTION

Mechanisms for the in vivo migration of cells across native tissue barriers have been studied through various in vitro assay methods devised to provide interaction between living cells and diverse tissue cultures. An important focal point of such research has been the evaluation of mechanisms by which metastatic cancer cells arising in glandular or squamous epithelium traverse native tissue barriers such as collagen/stroma barriers to enter the circulatory and lymphatic systems. Other studies in this area have been directed to migration of anti-inflammatory cells such as leukocytes from the blood vessels to the site of injury. Broadly, both the morphological and biochemical aspects of cellular migration are sought to be understood by appropriate bioassay techniques, with particular reference to histological migration routes, including mechanisms of tissue penetration and repair, and the role of chemoattractants in inducing migration through native tissue barriers. Another related area of investigation comprises the interaction of nonmigrating normal or malignant cells with these tissue barriers.

Known prior art bioassay methods for cellular interaction with native tissue barriers have generally proved to be unsatisfactory from a qualitative or quantitative standpoint, or both, primarily due to the tissues employed or their preparation. In conventional methods for in vitro assessment of cellular migration of tissues, whole tissue fragments of, for example, chick embryonic skin or mouse lung have been employed. Typically, these fragments are merely randomly cultured with the cellular material, making a reliable qualitative analysis of results difficult, and a quantitative analysis of results frequently impossible. For example, chick embryonic skin is commonly employed as the tissue medium in cellular migration assay techniques. This skin is a relatively thick complex of varying tissues, and includes native cellular components such as host-immune and inflammatory cells. Many of these tissue and cellular components are extraneous to in vivo cellular migration in humans, and serve only to impede or actively interfere with the mechanisms of interest. Chick embryonic skin is conventionally used in assays as tissue fragments intermixed with cells and a reliable evaluation of results is usually not possible without complete examination of each fragment, since sites of interaction of cells and tissue are not uniformly disposed over the tissue. Further, a quantitative analysis of tissue penetration cannot be made with chick embryonic skin and similar conventional tissues due to the thickness of the substrate and the presence of anomalous tissue. Other tissues commonly employed in similar assay techniques, including chick blastoderm, chick embryonic heart, chick embryonic mesonephros, chick wing bud, and extracted bovine articular cartilage, have similar disadvantages, including the major disadvantage of being of non-human origin. Known uses of human tissue, specifically human decidual tissue, have been relatively unsuccessful. While quantitative assay methods employing non-fragmented tissue have been developed, such known prior art methods have employed complex tissues of non-human origin. For example, radioactively labelled tumor cells have been cultured within the lunea of a perfused canine vein or cultured on chicken chorioallantoic membrane; the proportion of tumor cells which traverse these tissue barriers is calculated by measuring the radioactivity on either side of the barrier. Neither of these assay systems lends itself to the routine performance of assays on a useful scale; further, the chorioallantoic membrane contains a plurality of multicellular and connective tissue layers, and also is vascularized, so that host-immune cells are present.

It is accordingly an object of the present invention to provide an in vitro assay method for cellular interaction with natural tissue barriers wherein the tissue employed presents a normal connective tissue matrix barrier including attached intact cell layers.

It is another object of this invention to provide tissue for use in in vitro assay techniques for cellular interaction with normal tissue barriers which permits a reliable qualitative and quantitative analysis of the morphological and biochemical aspects of cellular interaction with native tissue barriers, including mechanisms of cellular penetration and repair and influences of chemotactic and chemokinetic factors.

It is a further object of the invention to provide a natural barrier tissue free from extraneous tissue and cellular components for use in in vitro assays which is readily available in large, uniform sheets as living tissue of human origin.

It is yet another object of this invention to provide a natural barrier tissue for in vitro assays of in vivo cellular migration which substantially duplicates native human tissue barriers.

It is an additional object of this invention to provide an in vitro qualitative and quantitative assay method for the identification and characterization of invasive cells, particularly malignant tumor cells, and also to provide diagnostic apparatus for use in the identification of metastatic tumor cells.

It is yet another object of this invention to provide a tissue of human origin readily available in the form of a large intact membrane for use as a substrate in the culture of normal cells.

Further objects and advantages of the invention will be apparent from the disclosure herein.

SUMMARY OF THE INVENTION

The invention comprises an in vitro assay method for the investigation of the mechanisms of cellular interaction with natural tissue barriers wherein the substrate tissue barrier comprises an amnion membrane. In exemplary embodiments, the invention comprises in vitro assay methods for quantitatively predicting the metastatic potential of a given tumor, and for screening anti-tumor drugs. In further exemplary embodiments, the invention comprises in vitro assay methods for the investigation of mechanisms of in vivo inflammatory cell migration, including responses to chemotactic factors, as well as a method for culturing non-migratory cells comprising interacting these cells with an amnion membrane growth substrate. The invention further comprises diagnostic apparatus for use in the assay method of the invention.

It has been found that the amnion membrane derived from the mammalian placenta provides an ideal experimental substrate for cellular activity in terms of both cellular growth and migration as well as availability and cost. As a medium for investigating the mechanisms of cellular interaction with native tissue barriers, the amnion has the advantage of presenting a normal connective tissue matrix barrier with associated intact cell layers. Thus, the characteristic in vivo barrier tissue structure comprising a continuous basement membrane disposed between a layer of epithelium and an underlayment of collagenous stroma can be presented in vitro as the amnion membrane. The use of the amnion membrane permits the generation of accurate and reliable test results, owing substantially to the lack of extraneous tissues, and, very importantly, to the unique avascular nature of the associated stroma, which precludes the presence of host blood antagonists such as leukocytes and white blood cells which tend to interfere with certain assays. Further, the physical structure of the amnion, comprising a large, transparent continuous sheet, permits both qualitative and quantitative analysis of cellular interaction with the substrate. Additionally, for assays involving human cells, it is highly desirable to employ a substrate tissue of human origin; this condition is well-satisfied by the use of the human amnion membrane, which is readily available at little or no cost as large sheets of living, disease-free human tissue.

BRIEF DESCRIPTION OF THE DRAWING

FIG. 1 is a transmission electron micrograph (1,000? magnification) of isolated human amnion membrane;

FIG. 3 is a perspective view of a diagnostic apparatus according to the present invention;

DETAILED DESCRIPTION OF THE INVENTION

Figure 2:
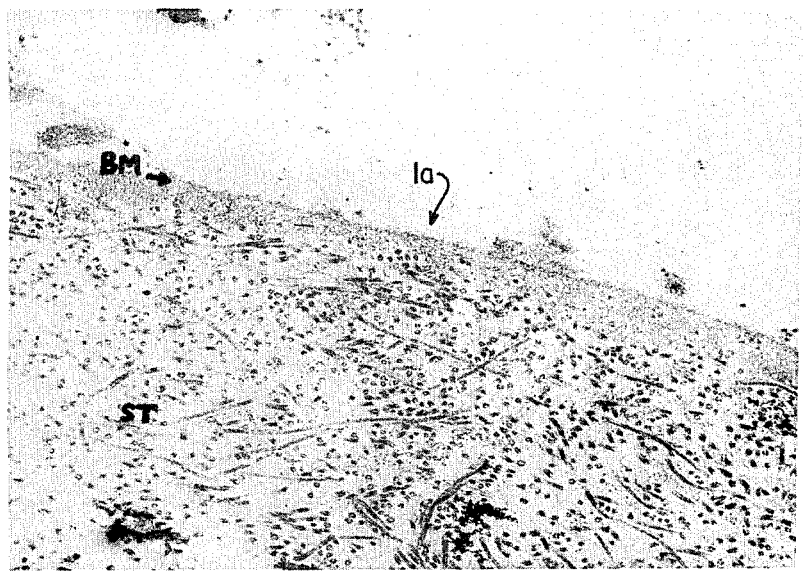
FIG. 2 is an electron micrograph (4000×) of isolated human amnion membrane with the surface denuded of epithelial cells.

The amnion membrane which is the subject of this invention is obtained from mammalian placenta by dissection from the chorion membrane by known methods; the integrity of the isolated amnion is then preferably verified by permeability and morphology studies. The resultant membrane is illustrated in FIG. 1, wherein an intact amnion, generally indicated at 1, is shown comprising an outer single layer of epithelium 2, and an intermediate continuous basement membrane layer 3 overlying a thin avascular connective tissue stroma 4 containing loosely bound collagen (not identified). In FIG. 2, the amnion 1a is shown with the basement membrane 3 partially denuded of the epithelium layer 2; the stroma 4 is intact.

The human amnion 1 illustrated in FIG. 1 is typical of mechanical barriers encountered in vivo by invading tumor cells. Two important extracellular matrix barriers are basement membrane and collagenous connective tissue stroma, which separate organ parenchymal cells from the associated blood vascular compartment; the basement membrane (BM) comprises extracellular matrixes composed of collagen type IV, glycoproteins, and glycosaminoglycans, and in vivo includes organ parenchymal cells attached to one side thereof and connective tissue stroma attached to the other side thereof. Thus, the human amnion membrane 1 of FIG. 1 effectively simulates a native tissue barrier comprising basement membrane 3 with attached connective tissue stroma 4. Further, the amnion 1 or 1a preserves the complex polarized architecture of the in vivo BM, presenting a continuous BM lamina densa attached to the epithelium layer 2 through the lamina lucida and to the collagenous stroma 4 through anchoring fibrils.

The amnion membranes useful in the practice of the present invention are derived from mammalian placenta, preferably after sufficient gestation to allow differentiation of the chorion and amnion layers in the fetal membrane, typically four to five months in humans. The amnion is employed either intact, as illustrated in FIG. 1, or as illustrated in FIG. 2, after being partially or wholly denuded of epithelium 2, by brief treatment with alkali or detergent. Generally, the intact amnion of FIG. 1 is particularly employed for barrier-penetration assays, whereas the denuded membrane 3 of FIG. 2 is particularly employed as a growth substrate for cell cultures.

In a preferred method of practicing the assay method of the invention, the amnion substrate barrier tissue is employed in the diagnostic apparatus of the invention.

One embodiment of this diagnostic apparatus is illustrated in FIG. 3, wherein the apparatus, generally indicated at 6, comprises an amnion chamber 7 including supporting means such as a holder 8 for supporting the amnion membrane 1 or 1a of FIG. 1 or 2. The membrane 1 or 1a divides the chamber into an upper compartment 9 and a lower compartment 10, with the epithelium 2 of the membrane 1 or 1a typically facing the upper compartment and the stroma 4 facing the lower compartment. The cellular material is placed in the upper compartment 9 on the amnion surface and sufficient time for interaction with the membrane 1 or 1a in the presence of an appropriate culture medium, is allowed to elapse. Conveniently, a plurality of chambers 7 are placed in cluster dishes of the type marketed by Costar, Inc. of Cambridge, Mass., containing culture media for cell growth, preferably a serum-free media supplemented with appropriate nutrients. In the illustrated embodiment, the holder 8 includes an upper ring 12 secured to a lower ring 13 by securing means such as bolts 14 for securing the upper ring 12 to the lower ring 13; the amnion 1 or 1a is clamped between the rings 12 and 13. The holder 8 is placed in a cluster dish 16 containing a fluid 17.

The embodiment of the apparatus 6 illustrated includes means for quantitative analysis of cellular penetration of the membrane, comprising a Millipore® filter 11 disposed against the stroma 4 of the membrane 1 or 1a for collecting cells which penetrate the full thickness of the membrane, which are subsequently counted. Other well-known analytical methods may be employed in conjunction with the apparatus 6 such as colorimetry or radioactive labelling. For example, the BM 3 can be radioactively labeled for use as a substrate in the assessment of degradative enzyme activity in tumor cells. Chemoattractants or other factors, if used, are generally placed in the lower compartment 10 of the chamber 7; in the illustrated apparatus, the fluid 17 would include the variable to be tested, such as a chemotactic factor or anti-tumor drug.

The amnion membrane 1 or 1a and the diagnostic apparatus of the invention are useful in in vitro assay methods for studying the interaction of a wide variety of cell types with the basement membrane surface. The invention is particularly useful for studying the mechanisms of invasion of metastatic tumor cells, a poorly-understood phenomenon. In vivo, circulating neoplastic cells, arrested in the capillary beds of an organ, invade the blood vessel walls and penetrate to extravascular tissues, where they establish metastases. In addition to the evaluation of the mechanisms by which metastatization proceeds, the invention permits the selection and recovery of invasive subpopulations of tumor cells from a primary neoplasm and the comparison of these subpopulations with non-invasive cells. Further, the effect of various drugs on the ability of tumor or other cells to penetrate native barrier tissue can be assessed.

The invention is further useful as an assay method for evaluating barrier tissue penetration by normal cells, such as inflammatory cell response to stimulus.

Polymorphonuclear leucocytes (PMN) are normal host inflammatory cells which migrate through host tissue barriers in response to inflammation.

In response to an inflammatory stimulus, the polymorphonuclear leucocytes adhere to the endothelial cell surface of post capillary venules, traverse the endothelium through interendothelial cell junctions and penetrate the basement membrane as they leave the vascular system to accumulate at the site of injury. A variety of substances induce PMN chemokinesis and chemotaxis, for example, N-formylmethionyl-leucylphenylalanine (FMLP) has been demonstrated to be one of the most potent chemoattractants for phagocytic cells. This substance exerts its activity by binding to specific cell receptors on PMN. FMLP increases PMN adhesiveness to endothelial cells and induces release of the granule bound enzymes. An optimal dose range exists for PMN chemotaxis by specific factors such as FMLP. At doses above the optimal range PMN homotypic aggregation is increased and migration is reduced. At doses below the optimal range both aggregation and migration are reduced.

The mechanism by which PMN penetrate whole endothelium is poorly understood because this process is difficult to study in vitro. Previous in vitro methods for investigating leukocyte migration and chemotaxis have utilized micropore filters, either alone or containing monolayers of cultured epithelial or endothelial cells. These previous systems are not optimal for simulating the actual physiological state because they do not include intact cell layers attached to normal continuous basement membrane, interfacing with connective tissue matrix, such as is presented by the amnion membrane.

In addition, the amnion membrane of the invention is highly useful as a growth substrate for various cell lines, some of which are difficult to culture by conventional methods. In general, the amnion is thus employed with the basement membrane denuded, as a sheet of tissue in conventional apparatus, in conjunction with a serum-free culture medium. Other culture media and substrate dispositions may be preferable, however, depending on the particular application.

The following Examples are illustrative of the practice of the present invention. In addition, the elaboration in *New Method for Preparing Large Surfaces of Intact Human Basement Membrane for Tumor Invasion Studies*, Liotta, et. al, Cancer Letters II (1980) 141–152, is incorporated herein by reference.

EXAMPLES

Example 1

Preparation of the Amnion Membrane

Normal term placentas were obtained fresh after delivery. The transparent amnion was aseptically peeled away from the chorion by blunt dissection and rinsed 2 times with PBS solution containing 0.02% sodium hypochlorite. Then the membrane was immersed in PBS containing penicillin-streptomycin (PS) (100 IU/ml and 100 $\mu$g/ml, respectively). Amnions were finally immersed in Minimal Essential Medium (with Earle's salts) with glutamine (4 mM) and PS. For experiments requiring a living epithelium, the amnion was used immediately. For experiments using a denuded BM surface, the epithelium was removed by treatment with alkali (0.14 ammonium hydrate for 15 min. @25° C.) and the amnions were stored under refrigeration. Morphologically, the human amnion membrane consists of a single layer of cuboidal to low columnar epithelial cells and basement membrane resting on nonvascular stroma; each epithelial cell is interlocked with its neighbor by numerous desmosomes. Ruthenium red staining demonstrates a prominent surface glycocalyx and epithelial microvilli. The epithelium is bound to the continuous basement membrane (BM) by numerous hemodesmosomes. The BM can be identified using periodic acid schiff staining or with immunohistology using antibodies to basement membrane components such as type IV collagen or lamina. The underlying stroma contains banded collagen fibers and fibroblasts; the stroma contains type I collagen, type V collagen, type III collagen and fibronectin. Even though the stroma connective tissue layer appears fibrillar, it forms a disease barrier impermeable to colloidal carbon particles and therefore does not contain preformed channels through which cells can passively migrate.

Preparation of the Diagnostic Apparatus

Two-compartment amnion chambers (FIG. 3) were constructed in the form of two Lucite rings. The rings measure 3.2 cm outside diameter and 1.2 cm inner diameter. The upper ring is 1.0 cm in height and the lower ring is 0.2 cm in height. Once clamped between the two rings, the amnion 1 or 1a divides the resulting chamber into upper compartment 9 and lower compartment 10. A Millipore filter (5 $\mu$m pore size, 2.3 cm diameter) was sandwiched in the chamber to be in direct contact with the amnion stromal surface 4. The chambers were placed in 6-well cluster dishes (Costar, Cambridge, Mass.). The amnions were verified to be free of leaks, by application of India ink to the denuded surface; mechanical tears or artificial effects caused by enzyme action result in immediate extravasation of carbon particles into the stroma with visually observable staining.

Example 2

PMN Migration Assay Method

In an exemplary chemotaxis assay, the chemoattractant N-formylmethionyl-leucyl-phenyl-alanine (FMLP) was introduced into the lower compartment 10 of the chamber 7. PMN were added to the upper compartment 9 onto the amnion epithelial layer 2 at the concentration of $1 \times 10^6$ cells in a total volume of 1.5 ml. The chambers containing the cells were incubated at 37° C. (5% $CO_2$, 95% air). Migration was observed periodically through an inverted microscope. Quantification of the cells which had traversed the full thickness of the amnion was done by staining the Millipore filter 11 with standard hematoxylin solution. PMN cells trapped within or adherent to the filter were easily identified against the white filter background. The whole filter (1.13 cm$^2$) was scanned (at 400× magnification) and the total number of cells were counted on each filter. The means and ranges were recorded for triplicate experiments using PMN obtained from the same donor. PMN were routinely counted on the filter 3 hours after their introduction into the upper compartment.

Figure 4:
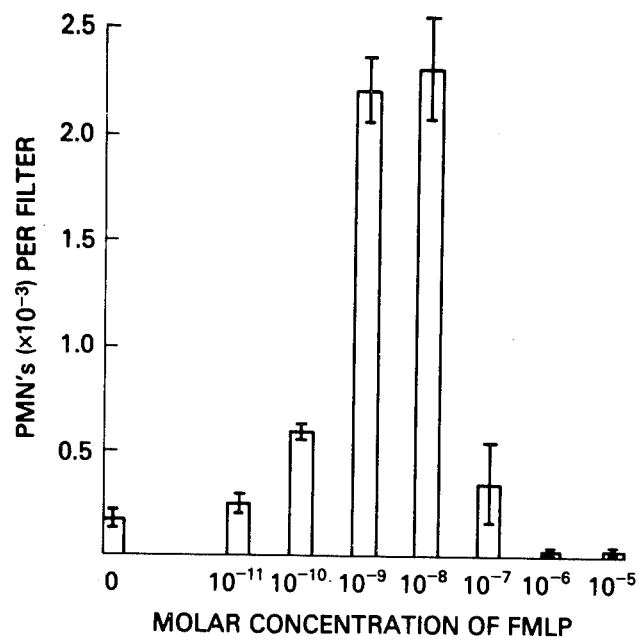
FIG. 4 is a graph wherein the presence of polymorphonuclear leucocytes (PMN) on the filter of the apparatus of FIG. 3 is related to the concentration of a chemoattractant (FMLP)
Figure 5:
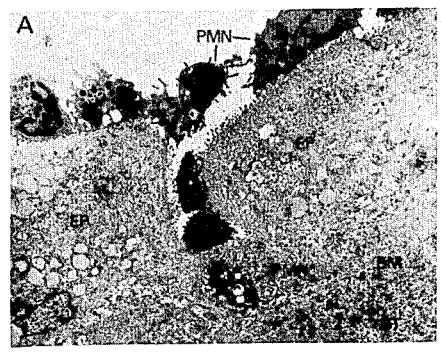
FIG. 5 is a photomicrograph (900× magnification) illustrating PMN invading the epithelial layer of the amnion membrane of FIG. 1 under influence of FMLP.
Figure 6:
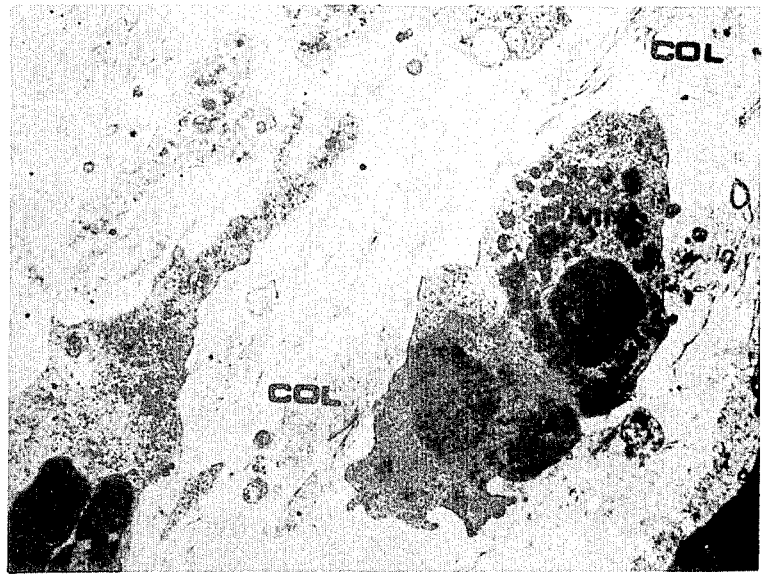
FIG. 6 is similar to FIG. 5, at a higher concentration of FMLP, PMN invading stroma collagen

The numbers of PMN which have traversed the amnion to enter the filters after 3 hours are shown in FIG. 4 for different concentrations of FMLP. Quantification of the FMLP dose-response indicated that an optimal rate of migration occurred at $10^{-6}$M and $10^{-9}$M concentration of FMLP applied to the bottom compartment. At FMLP $10^{-8}$M, the PMN were uniformly distributed as single cells and small aggregates (2–3 cells) at various stages of penetration within the epithelium (FIG. 5). PMN migration at this concentration was twelve-fold greater than spontaneous migration as detected without the addition of FMLP. At higher concentrations of FMLP ($10^{-5}$M, $10^{-6}$M) the PMN were noted to aggregate into large clumps (greater than 50 cells) and to remain tightly attached to the epithelial surface (FIG. 6). At FMLP $10^{-10}$M adherence of PMN was minimal or not different from the controls. Directed migration at low concentrations ($10^{-10}$–$10^{-12}$M) of FMLP showed only a three-fold increase over the controls. Thus, at a concentration of FMLP optimal for chemotaxis, aggregation on the epithelial surface was minimal. At greater than optimal concentration, PMN homotypic aggregation was pronounced and migration was markedly reduced. At suboptimal concentrations, PMN adherence to the epithelium was poor.

Example 3

Tumor Cell Migration Assay Method

Figure 7:
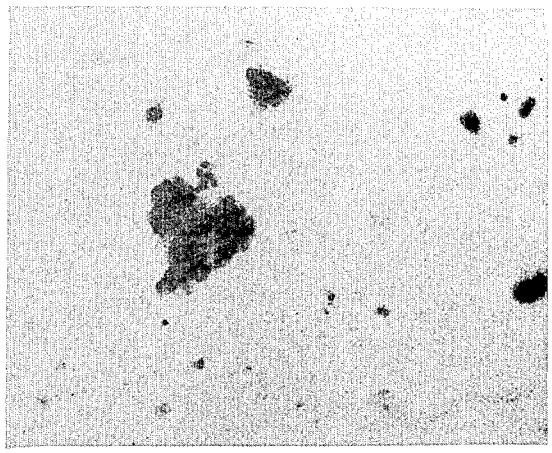
FIG. 7 is a photomicrograph (200× magnification) of MCF-7 breast carcinoma cells trapped in the filter of the apparatus of FIG. 3. The cells have penetrated the amnion of FIG. 1.
Figure 8:
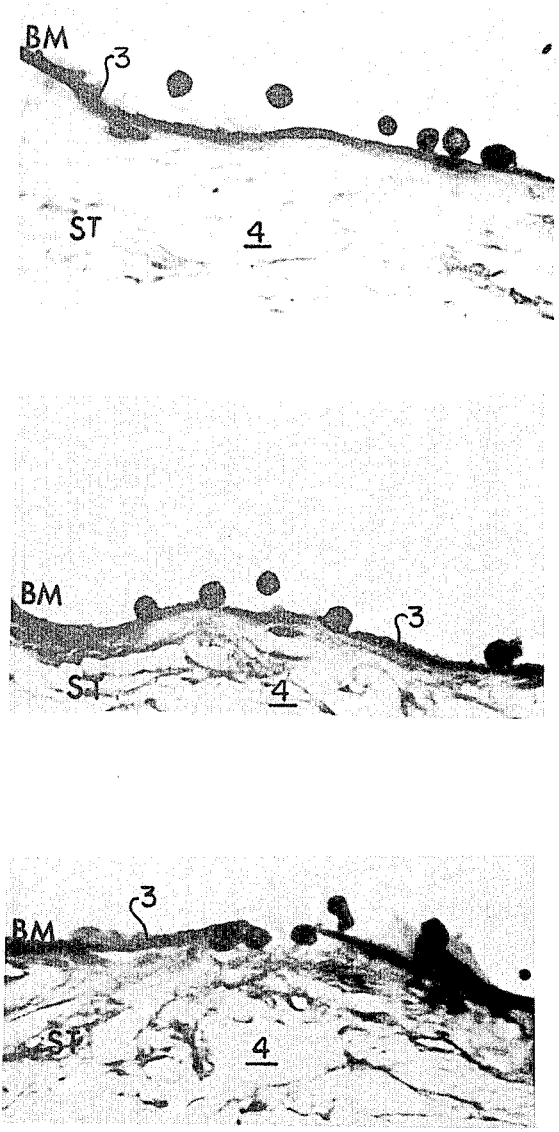
FIG. 8 is a photomicrograph (400× magnification) of human breast carcinoma cells penetrating the amnion of FIG. 2, over time.

The amnion invasion assay was used to study a variety of mirine and human tumor cell lines. Tumor cells grown in appropriate media were harvested from the log growth phase and washed in serum free media. The cells were then placed into the upper compartment 9 of the amnion chamber 7 of FIG. 3 ($2 \times 10^5$ cells, in 1.6 ml. DMEM with 0.14 fetuin), on the epithelial layer 2 of amnion 1. In contrast to the PMN which showed rapid adherence to the living epithelial surface, all tumor cells listed exhibited a poor adherence (approx. 20–40%) to the epithelium. When the epithelium was denuded, the tumor cells bound avidly (95–100%) to the intact basement membrane surface. Within 15 hours, highly invasive tumor cells penetrated the full thickness of the denuded basement membrane. Tumor cells penetrating the membrane were trapped in the Millipore® filter and grew slowly in the filter as small colonies (FIG. 7). Tumor cells were quantified on the filter as the total number of single cells and the total number of cell clumps or colonies. Time course studies (FIG. 8) suggested that most tumor cells traversed the amnion in single cell form and later grew as colonies on the filter. The number of tumor colonies on the filter increased with time as more tumor cells penetrated the amnion and reached the filter. Tumor cell colonies grown on the filter after penetrating the amnion could be subcultured. For MCF-7 breast carcinoma, MCF-7 cells cycled through the amnion once showed a five-fold increase in rate of invasion when they were again tested in the amnion assay. Human and bovine umbilical cord endothelium rapidly attached, and grew on the BM surface, even in the absence of serum or growth factors other than fetuin. The endothelial cells failed to invade the full thickness of the amnion up to 12 days in culture. Human fibroblasts or breast epithelium also failed to invade the amnion membrane. A summary of results for exemplary cell lines tested is given in Table I.

Example 4

Assay Method for Degradative Enzyme Activity in Tumor Cells

The amnion BM can be radio-labeled in organ culture. The labeled whole BM can then be used as a substrate for studying degradative enzyme activity in tumor cells.

Figure 9:
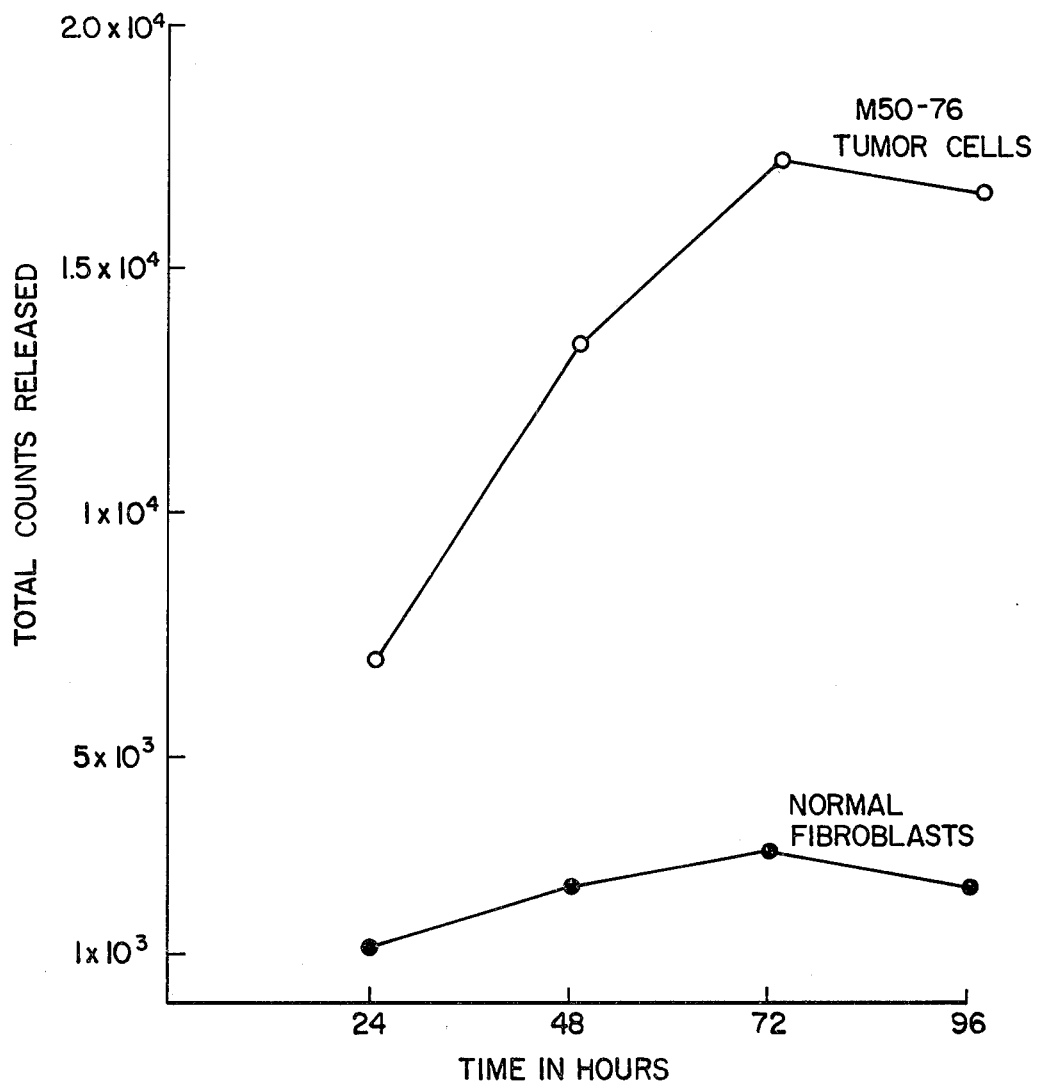
FIG. 9 is a graph comparing enzyme degradative activity on the amnion of FIG. 1 of tumor cells versus fibroblasts, as measured by release of radioactivity from the labelled amnion.

Whole, fresh amnion was preincubated for 1 hr. in media containing 20% dialyzed cell serum, sodium ascorbate (50 mg/ml), and beta amino proprionitrile (25 mg/ml). ($^{14}$C) proline 50 m i/ml was then added to the organ culture media and incubation was continued for 24 hrs. The $^{14}$C proline was incorporated into collagenous and noncollagenous components of the basement membrane as verified by extraction of the labeled type IV collagen and luminum, immunoprecipitation and collagenase digestion. M50-76 reticulum cell sarcoma cells were innoculated onto the ($^{14}$C) surface. Degradative activity was measured by the release of soluble radioactivity into the media. As shown in FIG. 9, the radioactivity in the media increased significantly with time. In contrast, fibroblasts did not cause significant release of radioactivity. By comparing the maximum radioactivity released by purified collagenase or plasmin with the maximum radioactivity released by the tumor cells, it was concluded that the tumor cells degraded both collagenous and glycoprotein components of the BM. Histologic studies of the M50 cell invasion of the amnion showed local thinning of the BM at the point of cell attachment, followed by penetration of the tumor cells through the BM into the stroma. The histologic observations and the release of radioactive substrate are in keeping with the hypothesis of local active degradation of the connective tissue matrix by the invading tumor cells. Tumor cells invaded the devitalized amnion connective tissue in vitro. Therefore, at least for the tumor cells studied here, active participation by living host cells is not required for tumor cell invasion.

Example 5

Plating Efficiency of Rat Hepatocytes on Human Amnion and Different Types of Collagen

|  | No. of Cells Attached | % of Total |
| --- | --- | --- |
| Basement membrane of human amnion | $1.4 \times 10^5$ | 46% |
| Stromal surface of human amnion | $6.6 \times 10^4$ | 22% |
| Type I collagen | $2.3 \times 10^4$ | 8% |
| Type II collagen | $3 \times 10^4$ | 10% |
| Type III collagen | $0.6 \times 10^4$ | 2% |
| Type IV collagen | $3.4 \times 10^4$ | 11% |
| Type V collagen | $0.2 \times 10^4$ | 1% |

Attachment was performed in serum free media.

The majority of hepatocytes are attached within 2 hours on the amnion.

Conclusion: Hepatocytes showed preferential attachment to whole amnion basement membrane surface as compared to the stromal surface of the amnion or attachment to dishes coated with different types of purified collagen. The amnion is a superior growth surface for hepatocytes.

TABLE I

Cultured cell lines tested in the amnion in vitro invasion assay.

I. Cells which fail to invade the full thickness of the amnion within 12 days.
  (a) human fibroblasts
  (b) human lymphocytes
  (c) human endothelial cells
  (d) human breast epithelium
  (e) bovine endothelium
  (f) rat hepatocytes II. Cells which invade the full thickness of the amnion within 2 days.
  (a) human MCF-7 breast carcinoma
  (b) human 2R75-1 breast carcinoma
  (c) human Ewings sarcoma
  (d) human osteosarcoma
  (e) human A431 squamous carcinoma
  (f) human polymorphonuclearleucocytes
  (g) mouse MSO-76 reticulum cell sarcoma
  (h) mouse BL6 (B16 variant) melanoma
  (i) mouse PMT sarcoma.

What is claimed is:

1. In an in vitro assay method for evaluating cellular interaction with natural barrier tissue of the type wherein living cells are interacted in vitro with a substrate tissue, the improvement comprising employing a mammalian amnion membrane as the substrate tissue.

2. The invention of claim 1, wherein the cellular interaction to be evaluated comprises cellular invasion or penetration of the natural barrier tissue.

3. The invention of claim 1, wherein the amnion is derived from a human placenta.

4. The invention of claim 3, wherein the cells are inflammatory cells and are interacted in the presence of a substance from a biological source.

5. The invention of claim 4, wherein the cells are polymorphonuclear leucocytes.

6. The invention of claim 1, wherein the living cells are malignant tumor cells.

7. The invention of claim 6, wherein the tumor cells are interacted in the presence of a pharmaceutical composition.

8. The invention of claim 1, wherein the cells are normal migratory cells.

9. The invention of claims 6 or 8, wherein the cells are interacted in the presence of a chemoattractant.

10. The invention of claim 1 wherein the amnion connective tissue components are radioactively labeled.

11. A method for culturing cells in vitro comprising interacting living cells with a mammalian amnion membrane growth substrate.

12. The invention of claim 11, wherein the cells are interacted with the growth substrate in the presence of a serum-free culture medium.

13. The invention of claim 12, wherein the cells are hepatocytes.

14. A diagnostic apparatus comprising a chamber including a mammalian amnion membrane dividing the chamber into upper and lower compartments, and support means for supporting the amnion membrane within the chamber.

15. The invention of claim 14, wherein the support means comprises an upper ring, a lower ring, and securing means for securing the rings to form said chamber, and wherein the amnion is clamped between said rings to divide the chamber into upper and lower compartments.

16. The invention of claims 1, 2, 3, 6, 8, 7, 4, 14, or 15, wherein the amnion membrane is wholly or partially denuded of its associated epithelium.

* * * * *